US008614190B2

(12) United States Patent
Peng et al.

(10) Patent No.: US 8,614,190 B2
(45) Date of Patent: *Dec. 24, 2013

(54) THERMAL RESPONSIVE COMPOSITION FOR TREATING BONE DISEASES

(75) Inventors: Shen-Hua Peng, Taoyuan County (TW); Hsin-Hsin Shen, Hsinchu County (TW); Liang-Yo Yang, Taipei (TW); Meng-Yow Hsieh, Taipei (TW); Pei-Shan Li, Taipei (TW); Wei-Lin Yu, Zhubei (TW); Tsai-Yu Lin, Changhua (TW); Po-Liang Lai, Changhua (TW); Jui-Sheng Sun, Taipei (TW); Chih-Hung Chang, Taipei (TW); Yi-Hung Lin, Jhubei (TW)

(73) Assignee: Industrial Technology Research Institute, Hsinchu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/172,776

(22) Filed: Jun. 29, 2011

(65) Prior Publication Data
US 2012/0010139 A1 Jan. 12, 2012

Related U.S. Application Data

(60) Provisional application No. 61/360,284, filed on Jun. 30, 2010.

(51) Int. Cl.
*A61P 19/08* (2006.01)
*A61K 38/18* (2006.01)
*A61K 31/74* (2006.01)
*C07K 14/51* (2006.01)
*C07K 14/475* (2006.01)

(52) U.S. Cl.
USPC ......... 514/16.7; 514/7.6; 514/8.8; 424/78.08; 424/78.17

(58) Field of Classification Search
None
See application file for complete search history.

(56) References Cited

U.S. PATENT DOCUMENTS

| 5,294,446 | A | 3/1994 | Schlameus et al. |
| 7,108,862 | B2 | 9/2006 | Remington et al. |
| 7,217,283 | B2 | 5/2007 | Pedrozo et al. |
| 7,309,232 | B2 | 12/2007 | Rutherford et al. |
| 7,323,445 | B2 | 1/2008 | Zhang et al. |
| 8,211,959 | B2 * | 7/2012 | Shen et al. ............ 523/522 |
| 2002/0015734 | A1 | 2/2002 | Uludag et al. |
| 2003/0158302 | A1 * | 8/2003 | Chaput et al. ............ 524/115 |
| 2006/0047088 | A1 | 3/2006 | Yamane et al. |
| 2007/0248675 | A1 | 10/2007 | Tae et al. |
| 2007/0259018 | A1 | 11/2007 | McKay |
| 2008/0206296 | A1 | 8/2008 | Bouler et al. |
| 2008/0233195 | A1 | 9/2008 | Spoorn et al. |
| 2008/0260714 | A1 | 10/2008 | Barry et al. |
| 2009/0053311 | A1 | 2/2009 | Soo et al. |
| 2009/0123547 | A1 | 5/2009 | Hill et al. |
| 2009/0124552 | A1 | 5/2009 | Hill et al. |
| 2009/0148487 | A1 | 6/2009 | Siedler et al. |
| 2009/0324669 | A1 | 12/2009 | Ogawa et al. |
| 2010/0028335 | A1 | 2/2010 | Lu et al. |
| 2010/0055078 | A1 | 3/2010 | Hughes-Fulford |
| 2010/0112014 | A1 | 5/2010 | Gilbert et al. |
| 2010/0166863 | A1 | 7/2010 | Shen et al. |

FOREIGN PATENT DOCUMENTS

| CN | 1965802 A | 5/2007 |
| EP | 1604693 A1 | 12/2005 |
| TW | 539718 B | 7/2003 |
| TW | 200516092 A | 5/2005 |
| TW | I247017 | 1/2006 |
| WO | 2008119053 A1 | 10/2008 |
| WO | 2010030244 A1 | 3/2010 |

OTHER PUBLICATIONS

Wozney J.M., Spine, 2002, vol. 27(16S):S2-S8.*
Kim et al., "Bone regeneration using hyaluronic acid-based hydrogel with bone morphogenic protein-2 and human mesenchymal stem cells", Elsevier, Biomaterials, 28 (2007) 1830-1837.
Asamura et al., "Bone Regeneration Using a Bone Morphogenetic Protein-2 Saturated Slow-Release Gelatin Hydrogel Sheet: Evaluation in a Canine Orbital Floor Fracture Model", Annals of Plastic Surgery vol. 64, No. 4, Apr. 2010, pp. 496-502.
Kempen et al., "Effect of local sequential VEGF and BMP-2 delivery on ectopic and orthotopic bone regeneration", Elsevier, Biomaterials 30 (2009) 2816-2825.
Yamamoto et al., "Enhanced bone regeneration at a segmental bone defect by controlled release of bone morphogenetic protein-2 from a biodegradable hydrogel", Tissue Engineering, vol. 12, No. 5, 2006, 1305-1311.
Takahashi et al., "Skull bone regeneration in nonhuman primates by controlled release of bone morphogenetic protein-2 from a biodegradable hydrogel", Tissue Engineering, vol. 13, No. 2, 2007, 293-300.
Lutolf et al., "Synthetic matrix metalloproteinase-sensitive hydrogels for the conduction of tissue regeneration: Engineering cell-invasion characteristics", PNAS, Apr. 29, 2003, vol. 100, No. 9, 5413-5418.
Betz et al., "Tissue response and orbital floor regeneration using cyclic acetal hydrogels", Journal of Biomedical Materials Research Part A, Jul. 9, 2008, 819-829.

(Continued)

*Primary Examiner* — Xiaozhen Xie
(74) *Attorney, Agent, or Firm* — Pai Patent & Trademark Law Firm; Chao-Chang David Pai

(57) ABSTRACT

Thermal responsive compositions for treating bone diseases are provided. The thermal responsive composition for treating bone diseases includes a bone growth factor and a biodegradable copolymer. The biodegradable copolymer has a structure of Formula (I) or Formula (II):

A-B-BOX-B-A        Formula (I)

B-A-B-(BOX-B-A-B)$_n$-BOX-B-A-B        Formula (II)

wherein, A includes a hydrophilic polyethylene glycol polymer, B includes a hydrophobic polyester polymer, BOX is a bifunctional group monomer of 2, 2'-Bis(2-oxazoline) and used for coupling the blocks A-B or B-A-B, and n is an integer and the same or more than 0.

20 Claims, 19 Drawing Sheets

(56) References Cited

OTHER PUBLICATIONS

Kang et al., "Repairing Defect and Preventing Collapse of Canine Femoral Head Using Titanium Implant Enhanced by Autogenous Bone Graft and rhBMP-2", Informa Healthcare, Connective Tissue Research, 48: 171-179, 2007.

Wang et al.,"Controlled-release of rhBMP-2 carriers in the regeneration of osteonecrotic bone", Elsevier, Biomaterials, 30 (2009) 4178-4186.

Benoit et al., "Synthesis and characterization of a fluvastatin-releasing hydrogel delivery system to modulate hMSC differentiation and function for bone regeneration", Biomaterials, 27 (2006) 6102-6110.

Kim et al., "Injectable in situ-Forming pH/Thermo-Sensitive Hydrogel for Bone Tissue Engineering", Tissue Engineering Part A, vol. 15, No. 4, 2009, 923-933.

Ho et al., "Bone Morphogenetic Protein 2 Acts via Inhibitor of DNA Binding Proteins to Synergistically Regulate Follicle-Stimulating Hormone $\beta$ Transcription with Activin A", Endocrinology, Jul. 2010, vol. 151, No. 7, 3445-3453.

Yu et al., "Biodegradable Poly($\alpha$-hydroxy acid) Polymer Scaffolds for Bone Tissue Engineering", Journal of Biomedical Materials Research B: Applied Biomaterials, Apr. 2010, vol. 93B, Issue 1, 285-295.

Office Action (Notice of First Examination Opinion) issued by China's State Intellectual Property Office on May 2, 2013, for the above-referenced application's counterpart application in China (Application No. 201110182361.9).

Office Action (Notice of Examination Opinion) issued by Taiwan's Intellectual Property Office on Nov. 8, 2013, for the above-referenced application's counterpart application in Taiwan (Application No. 100123025).

\* cited by examiner

THERMAL RESPONSIVE COMPOSITION FOR TREATING BONE DISEASES

CROSS REFERENCE TO RELATED APPLICATIONS

This application is related to and claims the benefit of the filing date of U.S. Provisional Patent Application No. 61/360,284, filed on Jun. 30, 2010, which provisional application is hereby incorporated herein by reference.

TECHNICAL FIELD

The disclosure relates to a thermal responsive composition, and in particular relates to a thermal responsive composition for treating bone diseases.

BACKGROUND

In most instances, a substitutive tissue must be used to recover the functionality of body tissue damaged by disease, unless the original tissues have a high inherent regeneration capacity. The unavailability of acceptable human donor organs, and the low rate of long term success thereof due to host versus graft rejection are the main challenges now facing the field of tissue and organ transplantation. In order to solve the above problems, biomaterials (such as synthetic or natural matrix serving as carriers) are provided to be implanted in the desired region to facilitate cell seeding.

According to medical statistics, approximately 30% of tissue reconstruction processes performed relates to bone tissue reconstruction. In recent years, biomaterials have been applied to reconstruct hard tissues and soft tissues of bone structures. For reconstruction of hard tissues, a key challenge is to facilitate fixation of bone fragments in an articular surface fracture or a comminuted fracture. Thus, a bone fixation device has been developed. The bone fixation device, such as a K-pin, bone nail, or cable or anchor, has a micro-textured contact surface to enhance installation or gripping characteristics thereof. For soft tissues, adherence to the bone fragments are peeled off before using bone fixation devices, thereby causing poor circulation of blood and increasing risk of nonunion fracture. In addition, when using bone fixation devices for soft tissues, bone fragments are further disintegrated following the surgical operation.

At present, most bone cements are primarily made of polymethyl methacrylate (PMMA). The bone cement can provide sufficient strength for a bone fracture at an early stage. Patients using the bone cement are not apt to develop allergies thereto due to the biologically inert properties thereof. Specifically, the bone cement is non-biodegradable. Therefore, the fixation of bone fragments using the bone cement is not a substantially complete bone union and the bone cement is not suitable for traumatic fractures. Further, other bones adjacent to the fixation of bone fragments may be broken by the bone cement due to the mechanical strength of the bone cement.

The fractures of 2-5% of patients do not heal at all, resulting in the condition known as "nonunion fracture". Generally, bone transplantation surgeries should be used for treating nonunion fractures; especially nonunion fractures due to abnormal blood flow patterns in the bone. For treating nonunion fracture, a patient receives two surgeries, wherein one is used to collect autologous tissues from the patient and the other is used to transplant and fix the autologous tissues to the affected region. Therefore, it is necessary to develop a graft substitute in place of the autologous tissues.

Further, a bone graft substitute can be applied in the ischemic necrosis of a femoral head, such as for the reconstruction of a hip joint. Avascular necrosis (AVN) is a disease, for young adults, resulting from the temporary or permanent loss of blood supply to bones. With early diagnosis, at least 75% of the patient with AVN can recover after treatment. Various treatments for AVN focus on salvaging the head of the femur or other bones or joints may be used, such as core decompression. A necrotic tissue is first removed and packed with an autologous cancellous bone, leaving room for the insertion of an autologous fibular graft with an autologous fibular graft vascular pedicle, wherein the peroneal vessels are attached to provide abundant blood flow to the head of a femur. An anastomosis is performed between the lateral circumflex vessels and the fibula vascular pedicle. Although the procedure is oftentimes successful in stabilizing the femoral head and providing blood flow to the femoral head, it carries the risk for donor sight morbidity. A bioadhesion can be used, combined with a drug, and implanted into the femoral head. With the degradation of the bioadhesion, the drug is gradually released, facilitating the regeneration of bones and veins.

Further, bioactive substance (e.g. drugs, growth factors, nucleic acids etc.) delivery is very important for biomedical applications such as tissue engineering, cell therapy and disease medical therapy. The materials for the delivery carriers must provide biocompatible and biodegradable properties for feasible implantation. Preferably, the material is a fluid ex vivo, so that it may be easily mixed with drugs and transformed into a gel after being injected into a body by a syringe, catheter or laparoscope for delivering the bioactive substances to the desired tissue area. After, the drugs are released over time, a therapeutic effect is achieved.

Currently, few delivery materials satisfy all requirements for body compatibility. There is, therefore, still a need for a thermal sensitive and biodegradable copolymer (serving as a delivery carrier or bone graft substitute to facilitate bone healing) for treating bone diseases

SUMMARY

The disclosure provides a thermal responsive composition for treating bone diseases. The composition includes a bone growth factor and a biodegradable copolymer. Particularly, the biodegradable copolymer has a structure represented by Formula (I) or Formula (II):

A-B-BOX-B-A                                                       Formula (I);

and

B-A-B-(BOX-B-A-B)$_n$-BOX-B-A-B             Formula (II), wherein, A includes a hydrophilic polyethylene glycol polymer, B includes a hydrophobic polyester polymer, BOX is a bifunctional group monomer of 2,2'-Bis(2-oxazoline) and used for coupling the blocks A-B or B-A-B, and n is an integer and the same or more than 0.

According to another embodiment of the disclosure, a method for the treatment of bone diseases is also provided, wherein the method includes: administering the thermal responsive composition of claim 1 to a subject suffering from bone diseases.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
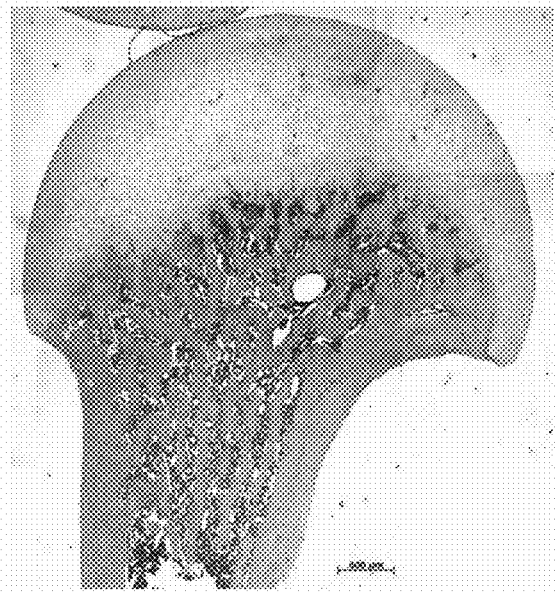
FIGS. 1-4 show tissue sections of the femur of the rats in the Groups Sham, NS, HG, and HG+BMP2, respectively.

The disclosure provides a thermal responsive composition for treating bone diseases including a bone growth factor, and a biodegradable copolymer. The composition of the disclosure shows thermal responsivity (sensitivity). Therefore, the composition behaves as a liquid at room temperature (in vitro), and the composition behaves a sol-gel at body temperature (in vivo). Namely, the composition can be transferred from a liquid drug delivery system to a sol-gel drug delivery system due to environmental temperatures. The sol-gel drug delivery system promotes enclosing the bone growth factor within the affected region and of near-linear controlled release of bone growth factor for an extended period of time for treatments.

The thermal responsive composition for treating bone diseases of the disclosure is biodegradable with no cytotoxicity after degradation, and the biodegradable copolymer is hydrolyzable and can be discharged harmlessly from the body through the urethra. Therefore, the composition does not need to be removed by additional operations. The thermal responsive composition for treating bone diseases of the disclosure promotes osteogenesis leading to facilitation of bone healing. The thermal responsive composition for treating bone diseases can serve as a carrier of an injection, pastille, powder, gel or oral liquid, and can be applied to the treatment of bone diseases such as the treatment of avascular necrosis (hip reconstruction), fractures, or osteoporotic fractures.

The thermal responsive composition for treating bone diseases of the disclosure includes a bone growth factor and a biodegradable copolymer. The bone growth factor can include bone morphogenetic protein, transforming growth factor-β, fibroblast growth factor, insulin-like growth factor, vascular endothelial growth factor, or combinations thereof. The bone morphogenetic protein can include BMP-1, BMP-2, BMP-3, BMP-4, BMP-5, BMP-6, BMP-7, BMP-8, BMP-9, BMP-10, BMP-11, BMP -12, BMP-13, BMP-14, BMP-15, BMP-16, BMP-17, BMP-18, BMP-19, BMP-20, BMP-21, or combinations thereof.

The biodegradable copolymer (acting as a hydrogel) can be a two-phase block copolymer represented by A-B-BOX-B-A or B-A-B-BOX-B-A-B, wherein A is a hydrophilic block such as a hydrophilic polyethylene glycol polymer, B is a hydrophobic block such as a hydrophobic polyester polymer, and BOX is a bifunctional group monomer of 2,2'-Bis(2-oxazoline). The biodegradable copolymer hydrogel is prepared by cross-linking the di-block A-B or the tri-block B-A-B via ring-opening polymerization in presence of a bifunctional group monomer (2,2'-Bis(2-oxazoline)).

An exemplary embodiment of a biodegradable copolymer hydrogel includes a copolymer represented by Formula (I):

A-B-BOX-B-A, wherein, A comprises a hydrophilic polyethylene glycol polymer, B comprises a hydrophobic polyester polymer, and BOX is bifunctional group monomer of 2,2'-Bis(2-oxazoline) for coupling the di-blocks A-B.

Another exemplary embodiment of a biodegradable copolymer hydrogel includes a copolymer represented by Formula (II):

B-A-B-(BOX-B-A-B)$_n$-BOX-B-A-B, wherein, A comprises a hydrophilic polyethylene glycol polymer, B comprises a hydrophobic polyester polymer, BOX is bifunctional group monomer of 2,2'-Bis(2-oxazoline) for coupling the tri-blocks B-A-B, and n is an integer, equal to or greater than 0.

The hydrophilic polyethylene glycol polymer (A) can be polyethylene glycol polymer or methoxy-poly(ethylene glycol). The hydrophilic polyethylene glycol polymer (A) can have a molecular weight of 300-1000. Further, the hydrophobic polyester polymer(B) can be polymers or copolymers derived from D,L-Lactide, D-Lactide, L-Lactide, D,L-Lactic acid, D-Lactic acid, L-Lactic acid, glycolide, β-propiolactone, δ-valerolactone, or ε-caprolactone, such as poly(lactide-co-glycolide) (PLGA), poly(propionic-co-lactic ) (PPLA), poly(valeric-co -lactic) (PVLA), or poly(caproic-co-lactic) (PCLA). The hydrophobic polyester polymer (B) can have a molecular weight of 500-5000. For example, the hydrophobic polyester polymer (B) can be poly(lactide-co-glycolide) which is a copolymer by polymizing the poly (lactic acid) and poly(glycolide acid), wherein the poly(lactic acid) has a mole percent of 50-90 mol% and the poly(glycolide acid) a mole percent of 10-50 mol%, based on the total mole percent of poly(lactic acid) and poly(glycolide acid).

In an embodiment of the disclosure, one end of the hydrophobic polyester polymer (B) which is not bonded with the hydrophilic polyethylene glycol polymer (A) can have an end capping/coupling functional group, wherein the hydrophobic polyester polymer (B) is bonded with the BOX via the end capping/coupling functional group. The end capping/coupling functional group can be derived from an end capping/coupling agent, wherein the end capping/coupling agent comprises an anhydride such as succinic anhydride, maleic anhydride, phthalic anhydride, or sebacic anhydride.

The thermal responsive composition for treating bone diseases of the disclosure is water-soluble. In low added amounts, the thermal responsive composition is apt to form polymeric micelles. In high added amounts (more than 10 wt %), the biodegradable copolymer exhibits reverse thermal gelation properties and has a low critical solution temperature of 10-90° C., or preferably 20-45° C. The biodegradable copolymer hydrogel behaves as a liquid with low viscocity below the critical solution temperature. After heating, the viscocity of the biodegradable copolymer hydrogen quickly rises, undergoing a reversible liquid-gel (or semi-solid) phase transition. It should be noted that, after long-period degradation, the hydrolysate of the thermal responsive composition is non-toxic since the hydrolysate has a pH value of more than 5.0.

In practical applications, first, the composition can be prepared by mixing water, bone growth factor, and biodegradable polymer under 5-10° C., behaving as an injectable solution. Next, the composition can be injected into the affected region of osteonecrosis, behaving as a sol-gel due to the human body temperature. The drug (bone growth factor) release rate can be controlled by the in vivo hydrolysis rate of the gel, facilitating bone healing. In some embodiments of the disclosure, the thermal responsive composition can be further mixed with ceramics, polymer, or metal and serve as a bone graft substitute with drug release in place of autologous tissues. The thermal responsive composition for treating bone diseases can serve as a carrier of an injection, pastille, powder, gel or oral liquid.

The following examples are intended to illustrate the disclosure more fully without limiting the scope of the disclosure, since numerous modifications and variations will be apparent to those skilled in this art.

Preparation of Biodegradable Copolymer

Example 1

A glass reactor (250 ml volume, 8 cm×8 cm×10 cm) connecting with a condenser, a heater, and a thermostat was provided, wherein educts of the condenser wrapped with heating tape looped back and rejoined to the reactor. 10.04 g of mPEG (methoxy poly(ethylene glycol)) (with a molecular weight of 550 g/mole), 20 g of lactide and 5.64 g of glycolide were added into the reactor, and the temperature was elevated slowly for complete dissolution. When the temperature reached and was sustained at 160° C., 14.0 μl of a catalyst (stannous 2-ethyl-hexanoate) was added. After stirring for 8 hrs, the mPEG-PLGA di-block was obtained.

Next, 1.84 g of succinic anhydride (with a molecular weight of 100.07 g/mole) was added into the reactor. After stirring for 4 hrs, 1.28 g of 2,2'-Bis(2-oxazoline) (with a molecular weight of 140.14 g/mole) was added into the reactor. After completely melting the mixture, stannous octoate as a catalyst was added into the reactor. After polymerizing for 4 hrs, the product was precipitated with diethyl ether/n-hexane (v/v=1/9) to form a translucent colloid. The residual monomers were washed three times and dried in a vacuum for 24 hrs at a temperature of 40° C., thus obtaining a biodegradable copolymer hydrogel (A) (the mPEG-PLGA di-block cross-linking by 2,2'-Bis(2-oxazoline)). The preparation procedure of the biodegradable copolymer hydrogel (A) is shown as below:

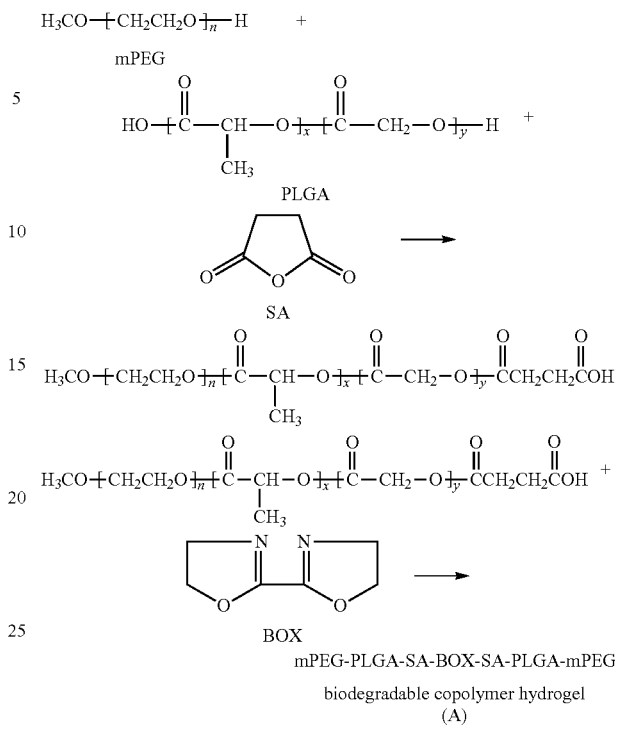

mPEG-PLGA-SA-BOX-SA-PLGA-mPEG
biodegradable copolymer hydrogel
(A)

$n>1$, $X>1$, $Y>1$

The molecule weight of the biodegradable copolymer hydrogel (A) was determined with a GPC, as shown in Table 1.

The biodegradable copolymer hydrogel (A) exhibited high temperature sensitivity. After measuring with a UV transmittancy test, the results showed that the biodegradable copolymer hydrogel (A) was a transparent liquid under a low temperature environment, a translucent viscous liquid at a temperature of 25° C., and an opaque immobile gel at a temperature of 40° C.

Example 2

A glass reactor (250 ml volume, 8 cm×8 cm×10 cm) connecting with a condenser, a heater, and a thermostat was provided, wherein educts of the condenser wrapped with heating tape looped back and rejoined to the reactor. 11.18 g of mPEG (methoxy poly(ethylene glycol)) (with a molecular weight of 550 g/mole), 20 g of lactide and 8.57 g of valerolactone were added into the reactor, and the temperature was elevated slowly for complete dissolution. When the temperature reached and was sustained at 160° C., 16.0 μl of a catalyst (stannous 2-ethyl-hexanoate) was added. After stirring for 8 hrs, the mPEG-PVLA di-block was obtained.

Next, 2.45 g of succinic anhydride (with a molecular weight of 100.07 g/mole) was added into the reactor. After stirring for 4 hrs, 1.71 g of 2,2'-Bis(2-oxazoline) (with a molecular weight of 140.14 g/mole) was added into the reactor. After completely melting the mixture, stannous octoate as a catalyst was added into the reactor. After polymerizing for 4 hrs, the product was precipitated with diethyl ether/n-hexane (v/v=1/9) to form a translucent colloid. The residual monomers were washed three times and dried in a vacuum for 24 hrs at a temperature of 40° C., thus obtaining a biodegradable copolymer hydrogel (B) (mPEG-PVLA di-block cross-linking by 2,2'-Bis(2-oxazoline)). The preparation procedure of the biodegradable copolymer hydrogel (B) is shown as below:

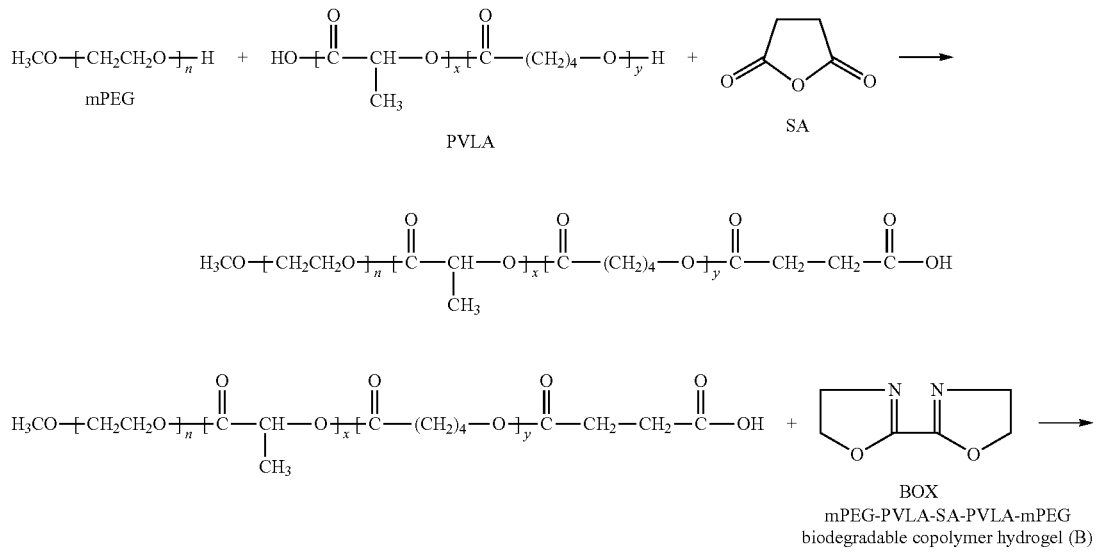

BOX
mPEG-PVLA-SA-PVLA-mPEG
biodegradable copolymer hydrogel (B)

n>1, X>1, Y>1

The molecule weight of the biodegradable copolymer hydrogel (B) was determined by a GPC, as shown in Table 1.

Example 3

A glass reactor (250 ml volume, 8 cm×8 cm×10 cm) connecting with a condenser, a heater, and a thermostat was provided, wherein educts of the condenser wrapped with heating tape looped back and rejoined to the reactor. 12.01 g of PEG (poly(ethylene glycol)) (with a molecular weight of 1000 g/mole), 25 g of lactide and 5.68 g of glycolide were added into the reactor, and the temperature was elevated slowly for complete dissolution. When the temperature reached and was sustained at 160° C., 17.07 μl of a catalyst (stannous 2-ethyl-hexanoate) was added. After stirring for 8 hrs, the PLGA-PEG-PLGA tri-block was obtained.

Next, 4.81 g of succinic anhydride (with a molecular weight of 100.07 g/mole) was added into the reactor. After stirring for 4 hrs, 3.06 g of 2,2'-Bis(2-oxazoline) (with a molecular weight of 140.14 g/mole) was added into the reactor. After completely melting the mixture, stannous octoate as a catalyst was added into the reactor. After polymerizing for 4 hrs, the product was precipitated with diethyl ether/n-hexane (v/v=1/9) to form a translucent colloid. The residual monomers were washed three times and dried in a vacuum for 24 hrs at a temperature of 40° C., thus obtaining a biodegradable copolymer hydrogel (C) (the PLGA-PEG-PLGA tri-block cross-linking by 2,2'-Bis(2-oxazoline)). The preparation procedure of the biodegradable copolymer hydrogel (C) is shown as below:

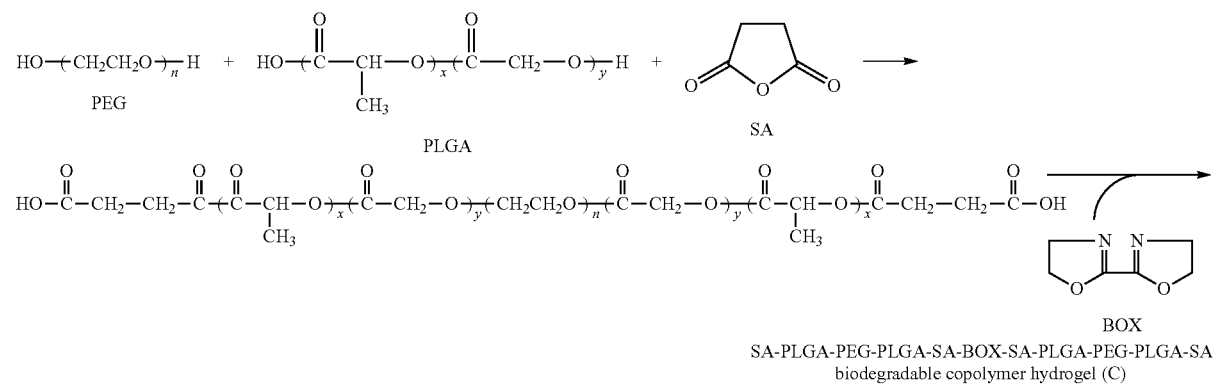

BOX
SA-PLGA-PEG-PLGA-SA-BOX-SA-PLGA-PEG-PLGA-SA
biodegradable copolymer hydrogel (C)

n>1, X>1, Y>1

The molecule weight of the biodegradable copolymer hydrogel (C) was determined by a GPC, as shown in Table 1.

The biodegradable copolymer hydrogel (C) exhibited high temperature sensitivity. After measuring by a UV transmittancy test, the results showed that the biodegradable copolymer hydrogel (A) was a transparent liquid under a low temperature environment, a translucent viscous liquid at a temperature of 25° C., and an opaque immobile gel at a temperature of 40° C.

Example 4

A glass reactor (250 ml volume, 8 cm×8 cm×10 cm)) connecting with a condenser, a heater, and a thermostat was provided, wherein educts of the condenser wrapped with heating tape looped back and rejoined to the reactor. 25 g of PEG (poly(ethylene glycol)) (with a molecular weight of 1000 g/mole), 25 g of lactide and 10.71 g of valerolactone were added into the reactor, and the temperature was elevated slowly for complete dissolution. When the temperature reached and was sustained at 160° C., 17.53 μl of a catalyst (stannous 2-ethyl-hexanoate) was added. After stirring for 8 hrs, the PVLA-PEG-PVLA tri-block was obtained.

Next, 1.78 g of succinic anhydride (with a molecular weight of 100.07 g/mole) was added into the reactor. After stirring for 4 hrs, 1.14 g of 2,2'-Bis(2-oxazoline) (with a molecular weight of 140.14 g/mole) was added into the reactor. After completely melting the mixture, stannous octoate as a catalyst was added into the reactor. After polymerizing for 4 hrs, the product was precipitated with diethyl ether/n-hexane (v/v=1/9) to form a translucent colloid. The residual monomers were washed three times and dried in a vacuum for 24 hrs at a temperature of 40° C., thus obtaining a biodegradable copolymer hydrogel (D) (PVLA-PEG-PVLA tri-block crosslinking by 2,2'-Bis(2-oxazoline)). The preparation procedure of the biodegradable copolymer hydrogel (D) is shown as below:

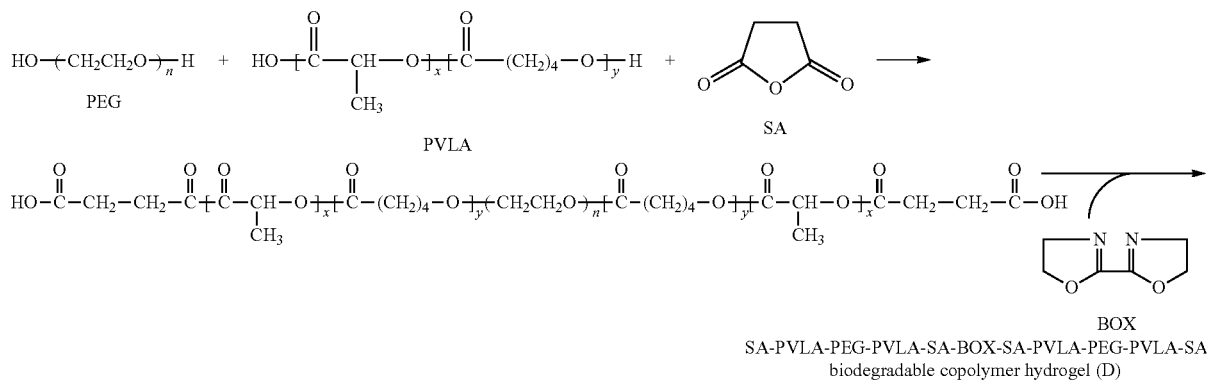

n>1, X>1, Y>1

The molecule weight of the biodegradable copolymer hydrogel (D) was determined by a GPC, as shown in Table 1.

TABLE 1

| Example | sample | Mw(g/mol) | Mw/Mn |
|---|---|---|---|
| 1 | biodegradable copolymer hydrogel (A) | 3917 | 1.46 |
| 2 | biodegradable copolymer hydrogel (B) | 4143 | 1.36 |
| 3 | biodegradable copolymer hydrogel (C) | 9401 | 1.23 |
| 4 | biodegradable copolymer hydrogel (D) | 8925 | 1.37 |

Comparative Example 1

A glass reactor (250 ml volume, 8 cm×8 cm×10 cm) connecting with a condenser, a heater, and a thermostat was provided, wherein educts of the condenser wrapped with heating tape looped back and rejoined to the reactor. 14.24 g of mPEG (methoxy poly(ethylene glycol)) (with a molecular weight of 550 g/mole), 25 g of lactide and 11.40 g of glycolide were added into the reactor, and the temperature was elevated slowly for complete dissolution. When the temperature reached and was sustained at 160° C., 20.24 μl of a catalyst (stannous 2-ethyl-hexanoate) was added. After stirring for 8 hrs, the mPEG-PLGA di-block was obtained. The preparation procedure of Comparative Example 1 is shown as below:

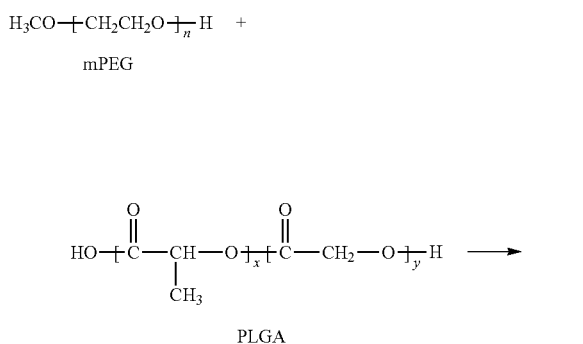

-continued

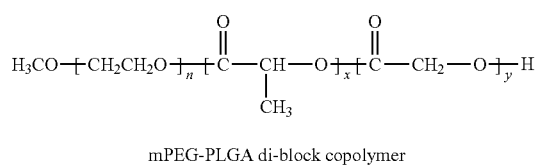

mPEG-PLGA di-block copolymer n>1, X>1, Y>1

Comparative Example 2

A glass reactor (250 ml volume, 8 cm×8 cm×10 cm) connecting with a condenser, a heater, and a thermostat was provided, wherein educts of the condenser wrapped with heating tape looped back and rejoined to the reactor. 7.12 g of PEG (poly(ethylene glycol)) (with a molecular weight of 1000 g/mole), 25 g of lactide and 11.36 g of glycolide were added into the reactor, and the temperature was elevated slowly for complete dissolution. When the temperature reached and was sustained at 160° C., 17.4 μl of a catalyst (stannous 2-ethylhexanoate) was added. After stirring for 8 hrs, the PLGA-PEG-PLGA tri-block was obtained. The preparation procedure of Comparative Example 2 is shown as below:

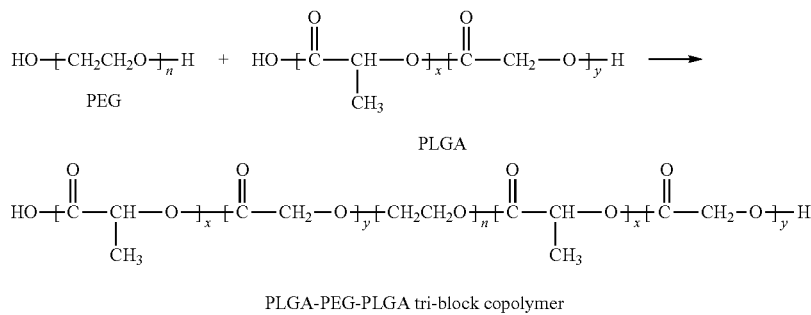

PLGA-PEG-PLGA tri-block copolymer n>1, X>1, Y>1

Measurement of Lower Critical Solution Temperature (LCST)

The biodegradable copolymer hydrogels (A)-(D) disclosed in Examples 1-4, the mPEG-PLGA di-block copolymer disclosed in Comparative Example 1 and the PLGA-PEG-PLGA tri-block copolymer disclosed in Comparative Example 2 were respectively measured by a lower critical solution temperature (LCST) test. The results are shown in Table 2.

TABLE 2

| Example | Sample | LCST (° C.) |
|---|---|---|
| Example 1 | biodegradable copolymer hydrogel (A) | 42.56 |
| Example 2 | biodegradable copolymer hydrogel (B) | 41.25 |
| Example 3 | biodegradable copolymer hydrogel (C) | 73.32 |
| Example 4 | biodegradable copolymer hydrogel (D) | 43.79 |
| Comparative Example 1 | mPEG-PLGA di-block | 25.09 |
| Comparative Example 2 | PLGA-PEG-PLGA tri-block | 35.41 |

As shown in Table 2, the biodegradable copolymer hydrogel (A) (the mPEG-PLGA di-block cross-linking by BOX) had an LCST of over 15° C. higher than that of the mPEG-PLGA di-block copolymer (as disclosed in Comparative Example 1), and the biodegradable copolymer hydrogel (C) (the PLGA-PEG-PLGA tri-block cross-linking by BOX) had an LCST of over 37° C. higher than that of the PLGA-PEG-PLGA tri-block copolymer (as disclosed in Comparative Example 2).

Preparation of Composition for Treating Bone Diseases

Example 5

A solution of the biodegradable copolymer hydrogel (A) of Example 1 dissolved in normal saline with a concentration of 15 wt % was prepared. Next, a bone growth factor BMP2 (bone morphogenetic protein-2) was added into the solution, obtaining a composition (A) for treating bone diseases (with a BMP2 concentration of 1 µg/ml).

Example 6

The biodegradable copolymer hydrogel (A) of Example 1 (1 g) was mixed with ceramic powder (0.5 g) and a bone growth factor BMP2 (bone morphogenetic protein-2), obtaining a composition (B) for treating bone diseases. Particularly, the ceramic powder consisted of tricalcium phosphate (TCP) and hydroxyapatite (HAP), wherein the ratio between TCP and HAP was 7:3 or 5:5 or 3:7.

Repair of Femoral Head

Example 7

Avascular necrosis (AVN) was successfully induced in the femoral head of 10-week-old female Wistar rats by double circumferential incision of the base of the femoral head followed by three consecutive daily intramuscular injections of methylprednisolone (MP, 20 mg/kg).

In the AVN model of the rats, the rats were divided into three groups and respectively treated with (1) injection of a normal saline (referred to as Group NS), (2) injection of a biodegradable copolymer hydrogel (A) of Example 1 (referred to as Group HG), and (3) biodegradable copolymer hydrogel (A) of Example 1 (HG)+BMP2 (referred to as Group HG+BMP2). Further, the Sham rats were provided for direct comparison (referred to as Group Sham).

Figure 3:
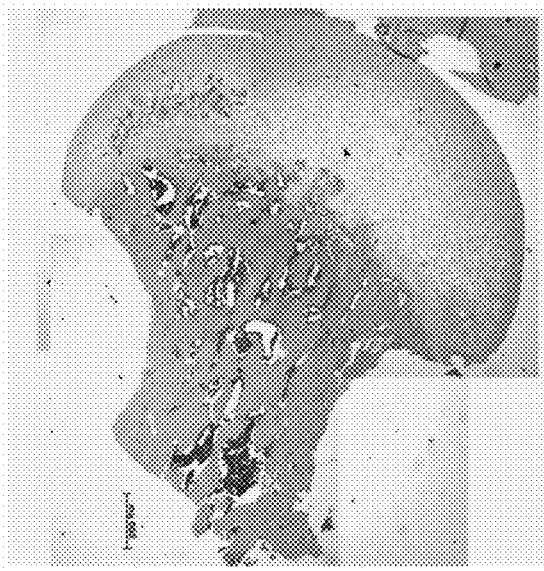
Figure 4:
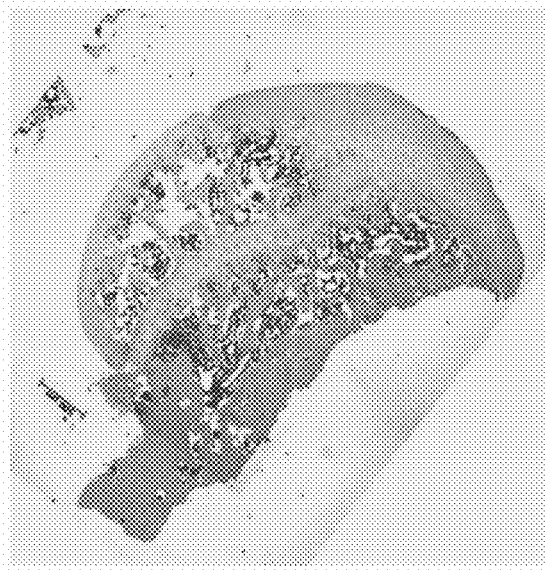

Eight weeks after the treatment, rats were sacrificed and femurs were removed and processed for examination of osteonecrosis (Yamamoto et al., 1995; Irisa et al., 2001; Miyanishi et al., 2002; Ichiseki et al., 2004). FIG. 1 shows the tissue section of the femur of the Sham rats, FIG. 2 shows the tissue section of the femur of the rats injected with normal saline, FIG. 3 shows the tissue section of the femur of the rats injected with biodegradable copolymer hydrogel (A) of Example 1 (HG)+BMP2, and FIG. 4 shows the tissue section of the femur of the rats injected with biodegradable copolymer hydrogel (A) of Example 1.

Figure 2:
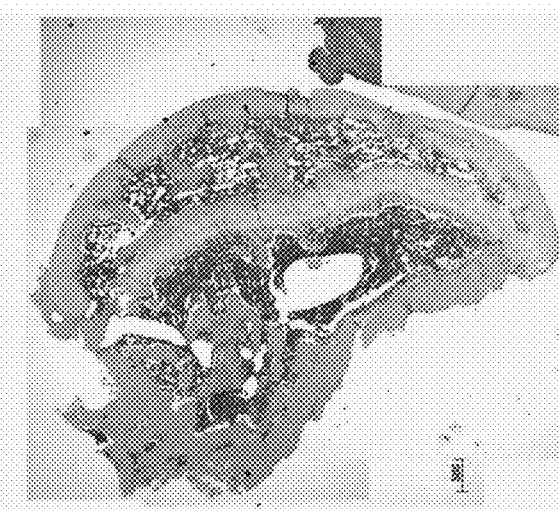

As shown in FIG. 2, AVN surgery drastically damaged the epiphysial cartilage of the femoral head and decreased the number and thickness of trabecula in the diaphysis (in comparison with FIG. 1). As shown in FIG. 3, the copolymer hydrogel plus BMP2 (Example 5) treatment seemed to attenuate the degree of avascular necrosis of the femoral head induced by AVN surgery and MP treatment in comparison with the AVN group receiving the normal saline treatment only (FIG. 2). As shown in FIG. 4, the femoral head of the AVN rats treated with copolymer hydrogel only showed a significant damage to the cartilaginous epiphysis and the number and thickness of trabecula in the diaphysis was reduced (in comparison with FIG. 3).

Figure 5:
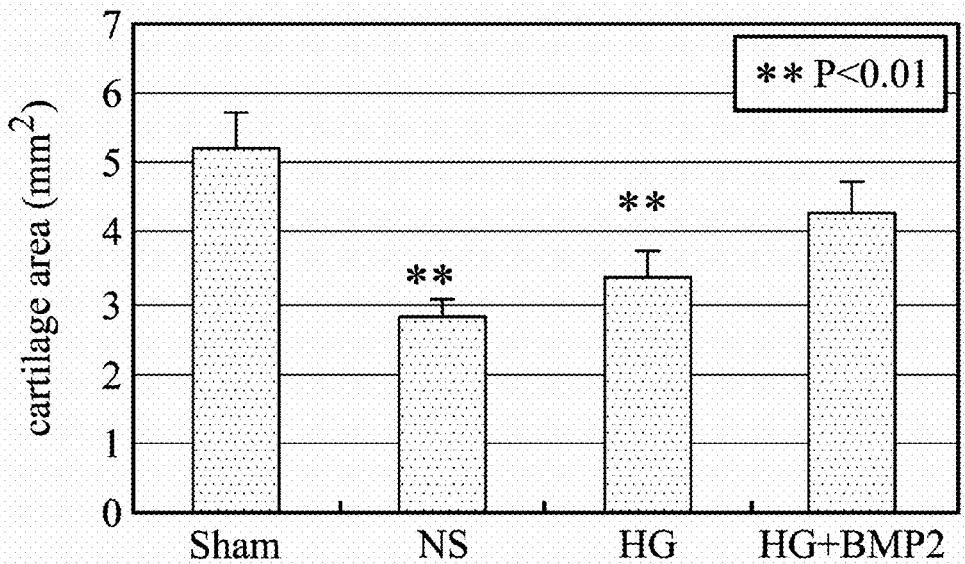
FIG. 5 shows a graph plotting the cartilage area of Groups NS, HG, HG+BMP2, and the Sham.
Figure 6:
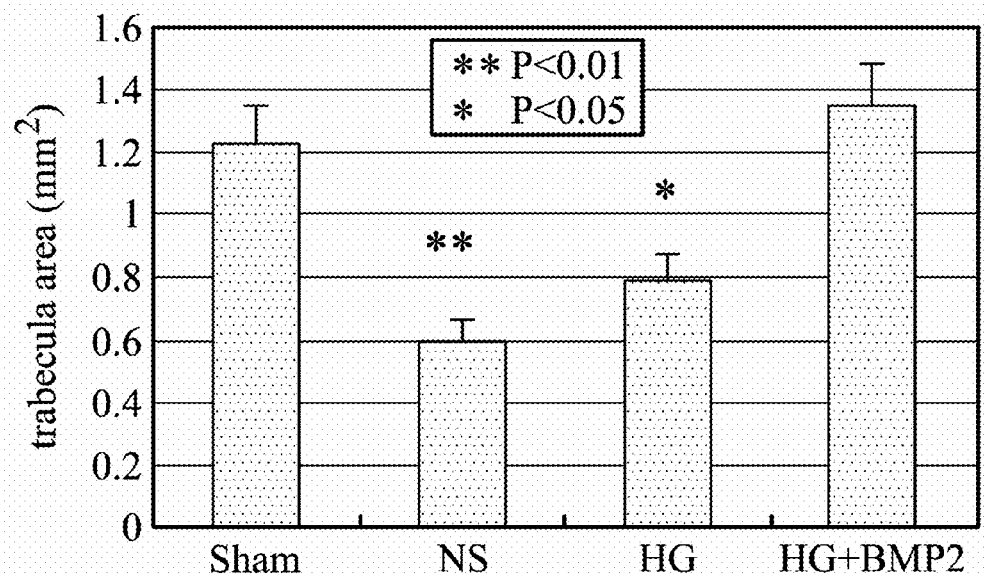
FIG. 6 shows a graph plotting the trabecula area of Groups NS, HG, HG+BMP2, and the Sham.
Figure 7:
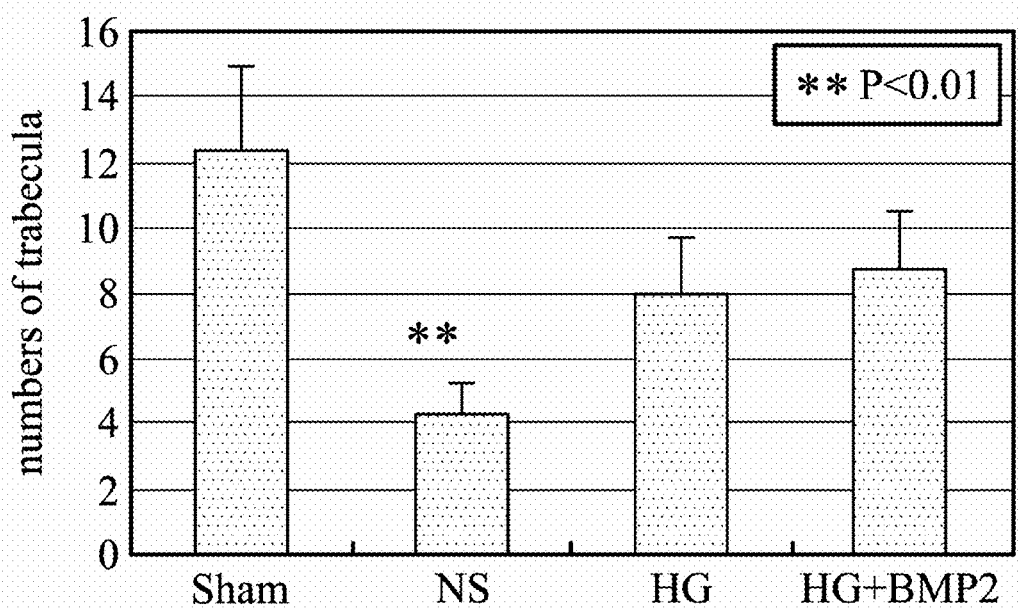
FIG. 7 shows a graph plotting the number of trabecula of Groups NS, HG, HG+BMP2, and the Sham.
Figure 8:
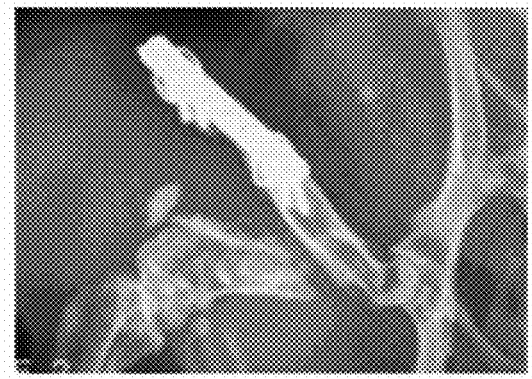
FIGS. 8-11 are a series of x-ray photographs showing the bone regeneration of the rabbits.
Figure 9:
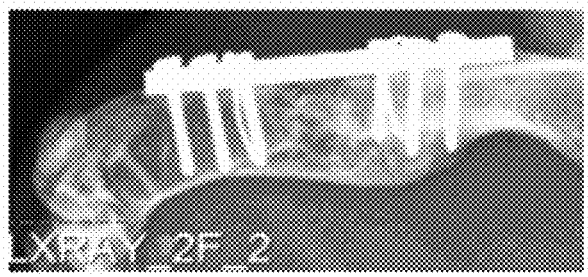
Figure 10:
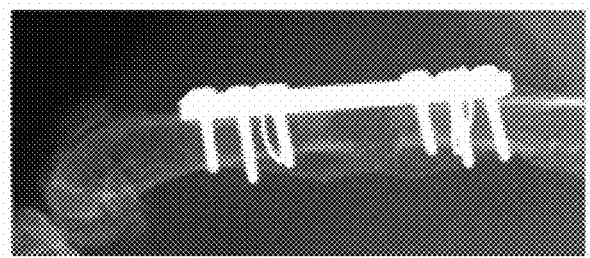
Figure 11:
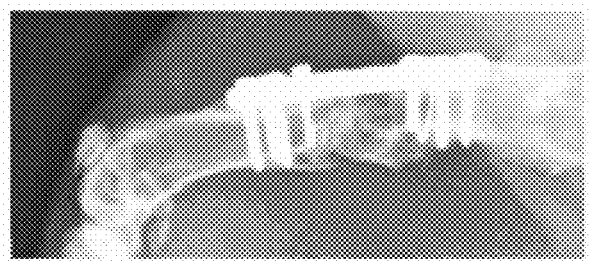
Figure 12:
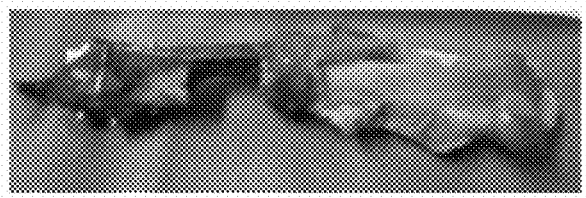
FIGS. 12-15 are a series of photographs showing the bone regeneration of the rabbits. (Experimental No. 712 is meaning auto-graft; Experimental No. 322 is the biodegradable copolymer hydrogel (A) of Example 1 was mixed with ceramic powder (HAp/TCP=7:3); Experimental No. 621 is the biodegradable copolymer hydrogel (A) of Example 1 was mixed with ceramic powder (HAp/TCP=5:5))
Figure 13:
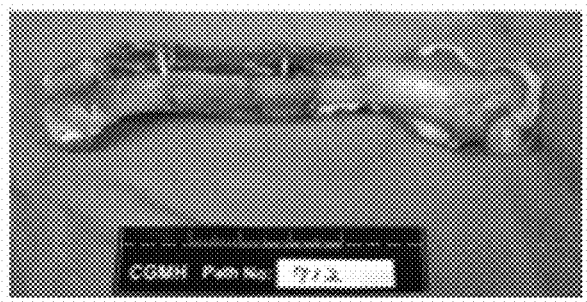
Figure 14:
Figure 15:

Further, FIG. 5 shows the cartilage area among Groups NS, biodegradable copolymer hydrogel (A) of Example 1 (HG), biodegradable copolymer hydrogel (A) of Example 1 (HG)+BMP2, and the Sham, FIG. 6 shows the trabecula area among Groups NS, HG, HG+BMP2, and the Sham, and FIG. 7 shows the number of trabecula among Groups NS, HG, HG+BMP2, and the Sham.

As shown in FIG. 5, the rats in the Groups NS and HG had obviously reduced cartilage areas in comparison with that of the rats in the Group Sham. Further, the rats in the Groups HG+BMP2 had a repaired cartilage area approximately equal to that of the rats in the Group Sham.

As shown in FIG. 6, the rats in the Groups NS and HG had obviously reduced trabecula areas in comparison with that of the rats in the Group Sham. Further, the rats in the Groups HG+BMP2 had a repaired trabecula area approximately equal to that of the rats in the Group Sham.

As shown in FIG. 7, the rats in the Groups NS and HG had obviously reduced number of trabecula in comparison with that of the rats in the Group Sham. Further, the rats in the Groups HG+BMP2 had a repaired number of trabecula approximately equal to that of the rats in the Group Sham.

Regeneration in Bone Defects with Graft Substitute

Example 8

Figure 16:
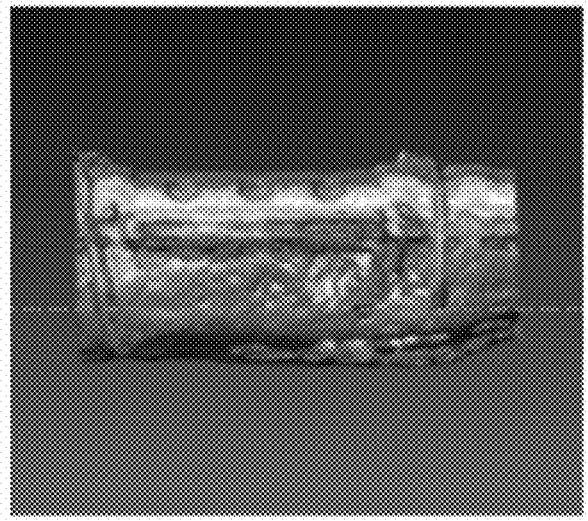
FIGS. 16-18 are a series of computed tomographs showing the bone regeneration of the rabbits.
Figure 17:
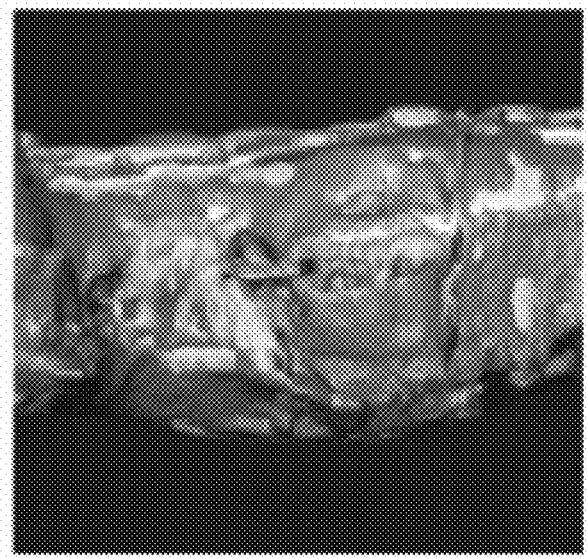
Figure 18:
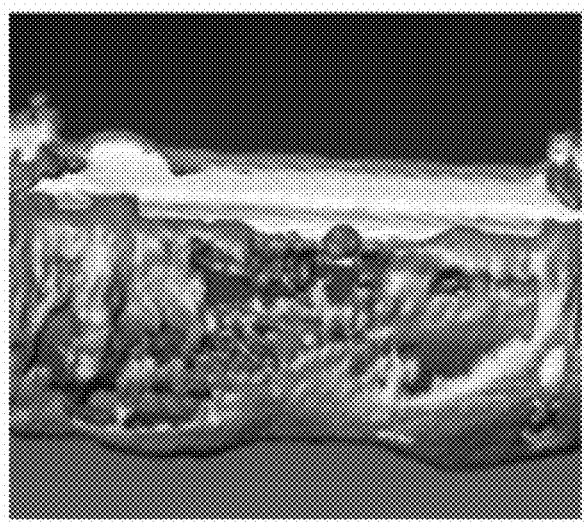

The composition (B) of Example 6 was injected into the bone defects of the rabbits, and the broken bones of the bone defects were refixed by nail-plate connections. The X-ray photographies of the bone defects were taken 12 weeks after implanted as shown in FIGS. 8-11 and bone defect, auto-graft, implant thermal hydrogel gel with ceramic powder (HAp/TCP=7:3), implant thermal hydrogel gel with ceramic powder (HAp/TCP=5:5), respectively. Three months after the treatment, rabbits were sacrificed and femurs were removed and processed for photography (as shown in FIGS. 12-15, bone defect, auto-graft, implant thermal hydrogel gel with ceramic powder (HAp/TCP=7:3), implant thermal hydrogel gel with ceramic powder (HAp/TCP=5:5), respectively) and computed tomography (as shown in FIGS. 16-18, bone defect, auto-graft, implant thermal hydrogel gel with ceramic powder (HAp/TCP=7:3), implant thermal hydrogel gel with ceramic powder (HAp/TCP=5:5), respectively). According to FIGS. 8-18, the aforementioned treatment (wherein the composition is served as a graft substitute) achieved a sufficient degree of bone regeneration similar to the treatment employing autologous bone tissues.

Example 9

A previously reported rat radial bone segmental defect model [Kruyt M C, et al. 2003; Lisignoli G, et al. 2002; Ozturk A M, et al. 2005] was used to evaluate bone regeneration in critical bone defects. 10-week-old female Wistar rats were divided into five groups. After sterile preparation, 5 mm segmental bone defects (with the periosteum left intact) in the radial shaft were created using a double-bladed diamond file on bilateral radii through 5 mm longitudinal incisions on the dorsal aspect of the forelimbs.

The osteotomy sites were treated with the following protocols: (1) Sham-operated group soaked with PBS (referred to as Group A); (2) Collagen sponges soaked with PBS (negative control, referred to as Group B) (3) Collagen sponges/biodegradable copolymer hydrogel (A) of Example 1 solution soaked with PBS (negative control, referred to as Group C); (4) Collagen sponges adding 8 μg, bone morphogenetic protein-2 (BMP-2) (positive control, referred to as Group D); and (5) Collagen sponges/biodegradable copolymer hydrogel (A) of Example 1 solution adding 8 μg, bone morphogenetic protein-2 (BMP-2) (referred to as Group E). The experiments performed in this study were approved by the Animal Ethics Committee, National Taiwan University Hospital, prior to the study and all animal experiments were carried out with adherence to the Committee guidelines. From previous experiments and the literature [Kruyt M C, et al. 2003, Suckow M A, et al. 1999]. All surgical procedures were performed with the rats under general anesthesia by intraperitoneal injection of tiletamine (25 mg/kg) and zolazepam (25 mg/kg, Zoletil) together with xylazine (10 mg/kg, Rompun). A single dose of cefazolin (20 mg/kg, administered intramuscularly) was used preoperatively for antibiotic prophylaxis. Animals were permitted full weight bearing and unrestricted movement upon awakening from anesthesia. Normal activity was resumed at the second day after surgery. Animals were killed by overdose anesthesia (thiopental 200 mg/kg IP) at 4 weeks, 8 weeks and 12 weeks.

Figure 19:
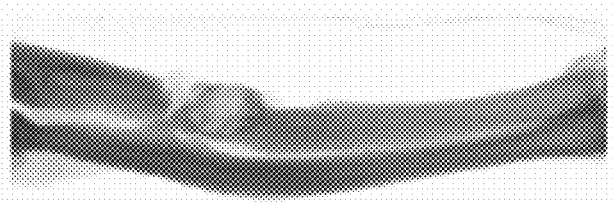
FIGS. 19, 21 and 26 are a series of x-ray photographs showing the bone regeneration of Group D of Example 9.
Figure 20:
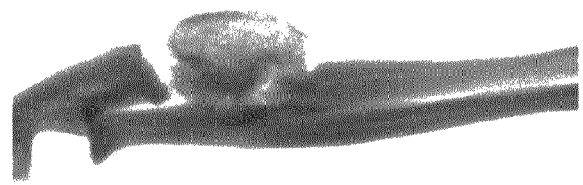
FIGS. 20, 22 and 27 are a series of x-ray photographs showing the bone regeneration of Group E of Example 9.
Figure 21:
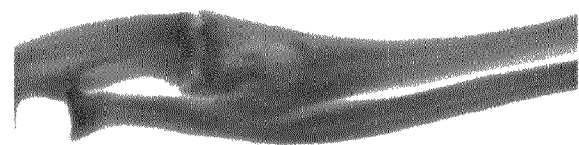
Figure 22:
Figure 23:
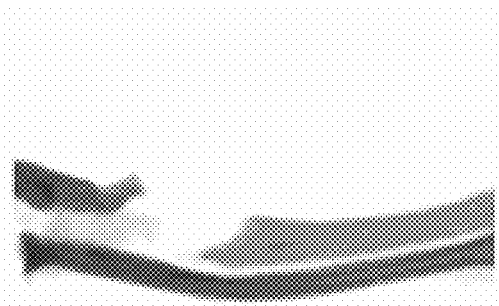
FIG. 23 is a x-ray photograph showing the bone regeneration of Group A of Example 9.
Figure 24:
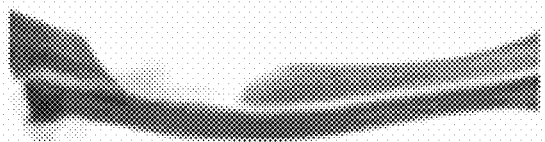
FIG. 24 is a x-ray photograph showing the bone regeneration of Group B of Example 9.
Figure 25:
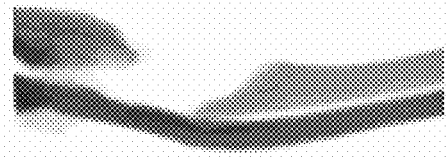
FIG. 25 is a x-ray photograph showing the bone regeneration of Group C of Example 9.
Figure 26:
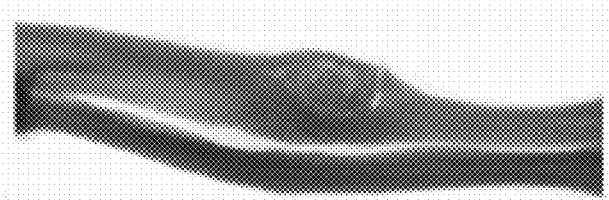
Figure 27:
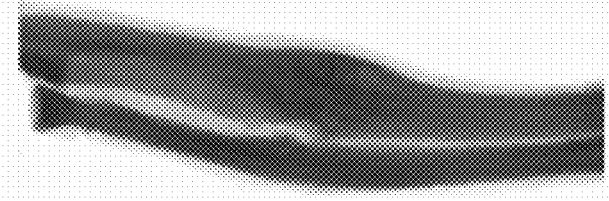

The X-ray photographies of the bone defects were taken 4 weeks after implanted as shown in FIGS. 19 (Group D) and 20 (Group E); the X-ray photographies of the bone defects were taken 8 weeks after implanted as shown in FIGS. 21 (Group D) and 22 (Group E); and the X-ray photographies of the bone defects were taken 12 weeks after implanted as shown in FIG. 23 (Group A), FIG. 24 (Group B), FIG. 25 (Group C), FIGS. 26 (Group D) and 27 (Group E). We observed the original 5 mm bone gap of negative control samples (group B and group C) maintained 5 mm (standard deviation, 1.02 mm); while the positive control samples (group D) were 0 mm (solid union). In this study, the sample size was determined based on a difference of radiographic measurements of bone gaps with a power of 80%, two-tailed, and a confidence interval of 95%. This resulted in a minimum of three samples per group for histologic evaluation.

Accordingly, the composition for treating bone diseases of the disclosure shows thermal responsivity. Therefore, the composition behaves as a liquid at room temperature (in vitro), and the composition behaves a sol-gel at body temperature (in vivo). The sol-gel drug delivery system is capable of fixation bone growth factor within the affected region and of near-linear controlled release of bone growth factor for an extended period of time for treatments. The composition for treating bone diseases can serve as a carrier of an injection, pastille, powder, gel or oral liquid, and can be applied to the treatment of bone diseases such as the treatment of avascular necrosis (hip reconstruction), fractures, or osteoporotic fractures.

Figure 28:
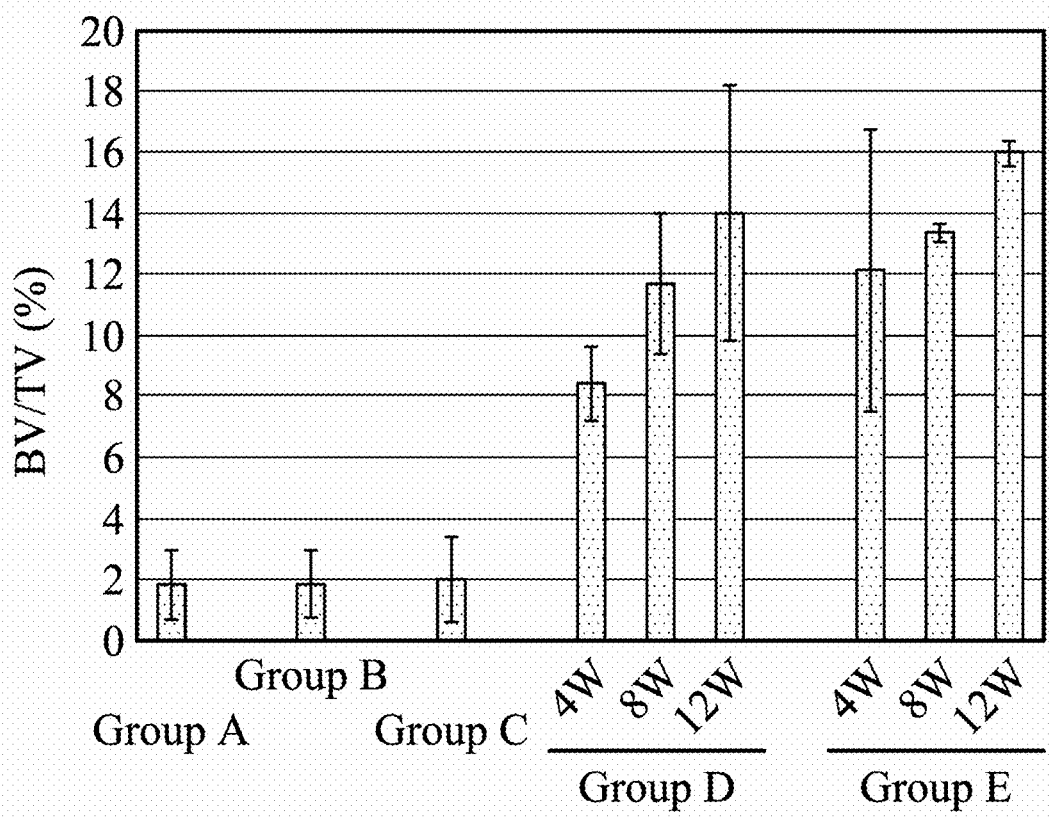
FIG. 28 shows the bone volume measurement (BV/TV) data of Example 9.
Figure 29:
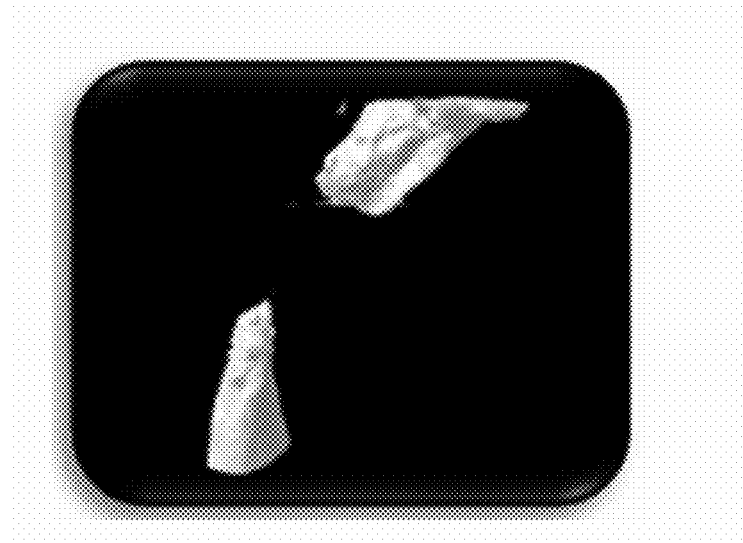
FIGS. 29, 30, and 31 are micro-CT images respectively of Group A, Group B, and Group C of Example 9.
Figure 30:
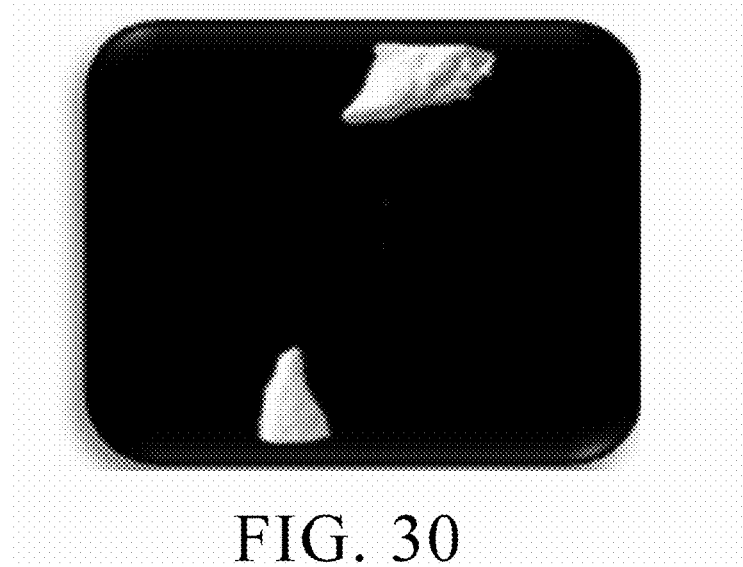
Figure 31:
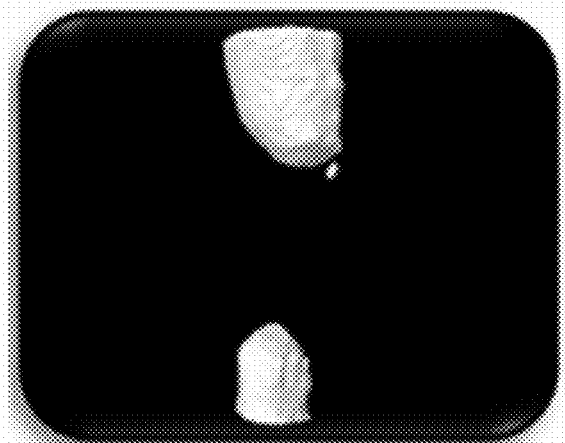
Figure 32:
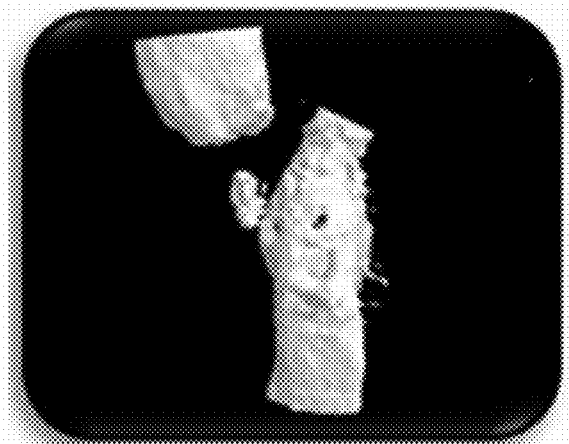
FIGS. 32-34 are a series of micro-CT images showing the bone regeneration of Group D of Example 9.
Figure 33:
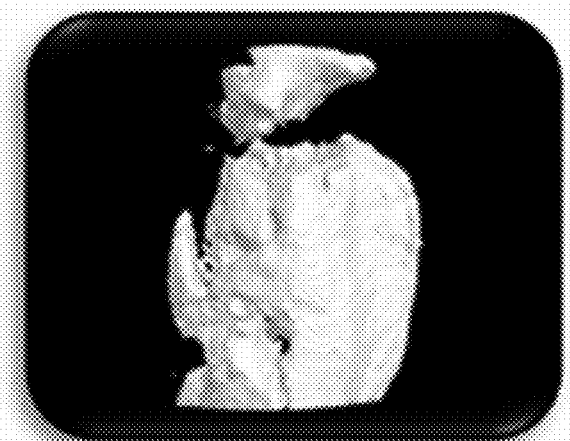
Figure 34:
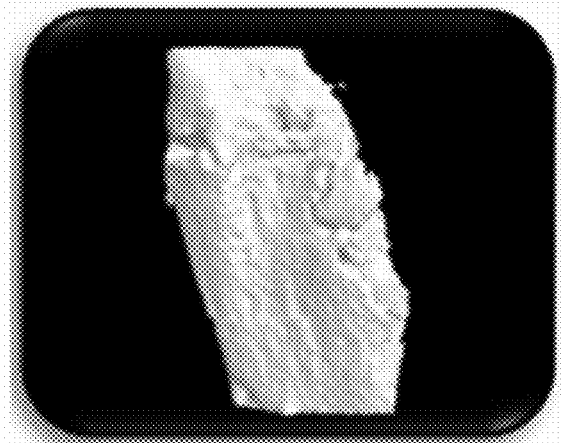
Figure 35:
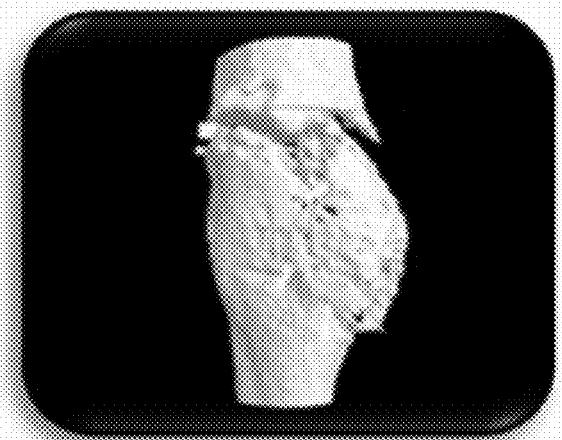
FIGS. 35-37 are a series of micro-CT images showing the bone regeneration of Group E of Example 9.
Figure 36:
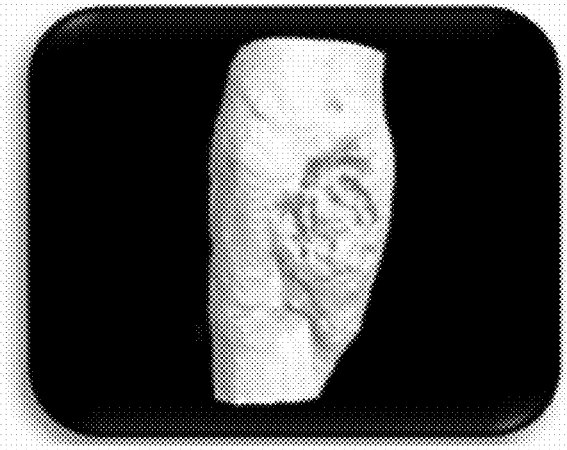
Figure 37:

As shown in FIG. 28, the bone volume measurement (BV/TV) data (quantified based on micro-CT images as shown in figures) showed the new bone formation of the critical-size defect site for each group (n=6). There is no difference of bone volume on Group A (Sham-operated, the micro-CT image of Group A is shown in FIG. 29), Group B (Collagen only group, the micro-CT image of Group B is shown in FIG. 30), and Group C (Collagen/biodegradable copolymer hydrogel (A) of Example 1 solution Only group, the micro-CT image of Group C is shown in FIG. 31) for 4 weeks, 8 weeks and 12 weeks. The bone volume fraction increased over time in Group D (Col+BMP-2 and Col/BOX+BMP-2, FIGS. 32-34 are micro-CT images of Group D which were taken respectively after 4 weeks, 8 weeks, and 12 weeks), and there is higher increase in Group E (Col/BOX+BMP-2 group, FIGS. 35-37 are micro-CT images of Group D which were taken respectively after 4 weeks, 8 weeks, and 12 weeks) than Group D.

While the disclosure has been described by way of example and in terms of preferred embodiment, it is to be understood that the disclosure is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A thermal responsive composition for treating bone diseases, comprising:
    a biological activity factor, wherein the biological activity factor is a bone growth factor, hydroxyapatite (HAp), tri-calcium phosphate (TCP), demineralized bone matrix (DBM), or combinations thereof; and
    a biodegradable copolymer, wherein the biodegradable copolymer has a structure represented by Formula (I):

A-B-BOX-B-A   Formula (I)

wherein, A comprises a hydrophilic polyethylene glycol polymer, B comprises a hydrophobic polyester polymer, and BOX is a bifunctional group monomer of 2, 2'-Bis (2-oxazoline) and used for coupling the blocks A-B.

2. The thermal responsive composition for treating bone diseases as claimed in claim 1, wherein an end of the hydrophobic polyester polymer (B) which is not bonded with the hydrophilic polyethylene glycol polymer (A) has an end capping/coupling functional group.

3. The thermal responsive composition for treating bone diseases as claimed in claim 2, wherein the hydrophobic polyester polymer (B) is bonded with the BOX via the end capping/coupling functional group.

4. The thermal responsive composition for treating bone diseases as claimed in claim 2, wherein the end capping/coupling functional group is derived from an end capping/coupling agent, and the end capping/coupling agent comprises an anhydride.

5. The thermal responsive composition for treating bone diseases as claimed in claim 4, wherein the end capping/coupling agent comprises succinic anhydride, maleic anhydride, phthalic anhydride, or sebacic anhydride.

6. The thermal responsive composition for treating bone diseases as claimed in claim 1, wherein the hydrophilic polyethylene glycol polymer (A) comprises methoxy-poly(ethylene glycol) (mPEG).

7. The thermal responsive composition for treating bone diseases as claimed in claim 1, wherein the hydrophobic polyester polymer (B) comprises polymers or copolymers derived from D,L-Lactide, D-Lactide, L-Lactide, D,L-Lactic acid, D-Lactic acid, L-Lactic acid, glycolide, β-propiolactone, δ-valerolactone, or ε-caprolactone.

8. The thermal responsive composition for treating bone diseases as claimed in claim 1, wherein the hydrophobic polyester polymer (B) comprises poly(lactide-co-glycolide) (PLGA), poly(propionic-co-lactic) (PPLA), poly(valeric-co-lactic) (PVLA), or poly(caproic-co-lactic) (PCLA).

9. The thermal responsive composition for treating bone diseases as claimed in claim 1, wherein the bone growth factor comprises bone morphogenetic protein, transforming growth factor β, fibroblast growth factor, insulin-like growth factor, vascular endothelial growth factor, or combinations thereof.

10. The thermal responsive composition for treating bone diseases as claimed in claim 9, wherein the bone morphogenetic protein comprises BMP-2, BMP-3, BMP-4, BMP-5, BMP-6, BMP-7, BMP-8, or combinations thereof.

11. The thermal responsive composition for treating bone diseases as claimed in claim 1, wherein the ratio of hydroxyapatite (HAp) and tri-calcium phosphate (TCP) is 7:3 to 5:5.

12. The thermal responsive composition for treating bone diseases as claimed in claim 1, wherein the thermal responsive composition for treating bone diseases is formulated as an injectable form, pastille, powder, gel or oral liquid.

13. A method for the treatment of bone diseases, comprising:
    locally administering the thermal responsive composition of claim 1 to a subject suffering from bone diseases.

14. The method as claimed in claim 13, wherein an end of the hydrophobic polyester polymer (B) which is not bonded with the hydrophilic polyethylene glycol polymer (A) has an end capping/coupling functional group.

15. The method as claimed in claim 13, wherein the hydrophilic polyethylene glycol polymer (A) comprises methoxy-poly(ethylene glycol) (mPEG).

16. The method as claimed in claim 13, wherein the hydrophobic polyester polymer (B) comprises polymers or copolymers derived from D,L-Lactide, D-Lactide, L-Lactide, D,L-Lactic acid, D-Lactic acid, L-Lactic acid, glycolide, β-propiolactone, δ-valerolactone, or ε-caprolactone.

17. The method as claimed in claim 13, wherein the bone growth factor comprises bone morphogenetic protein, transforming growth factor β, fibroblast growth factor, insulin-like growth factor, vascular endothelial growth factor, or combinations thereof.

18. The method as claimed in claim 17, wherein the bone morphogenetic protein comprises BMP-2, BMP-3, BMP-4, BMP-5, BMP-6, BMP-7, BMP-8, or combinations thereof.

19. The method as claimed in claim 13, wherein the ratio of hydroxyapatite (HAp) and tri-calcium phosphate (TCP) is 7:3 to 5:5.

20. The method as claimed in claim 13, wherein the thermal responsive composition for treating bone diseases is formulated as an injectable form, pastille, powder, gel or oral liquid.

* * * * *